(12) United States Patent
Martins

(10) Patent No.: US 11,246,748 B2
(45) Date of Patent: Feb. 15, 2022

(54) APPLICATOR DEVICE AND RELATED APPARATUS

(71) Applicant: CRYOTECH NORDIC AS, Vääna (EE)

(72) Inventor: Jean-Patrick Martins, Tallinn (FI)

(73) Assignee: CRYOTECH NORDIC AS, Vääna (EE)

( * ) Notice: Subject to any disclaimer, the term of this patent is extended or adjusted under 35 U.S.C. 154(b) by 0 days.

(21) Appl. No.: 17/277,017

(22) PCT Filed: Sep. 17, 2019

(86) PCT No.: PCT/EP2019/074838
§ 371 (c)(1),
(2) Date: Mar. 17, 2021

(87) PCT Pub. No.: WO2020/058255
PCT Pub. Date: Mar. 26, 2020

(65) Prior Publication Data
US 2021/0315732 A1    Oct. 14, 2021

(30) Foreign Application Priority Data

Sep. 18, 2018 (FI) ...................................... 20185775

(51) Int. Cl.
*A61F 7/00* (2006.01)
*A61N 5/06* (2006.01)

(52) U.S. Cl.
CPC .......... *A61F 7/0085* (2013.01); *A61N 5/0616* (2013.01); *A61F 2007/003* (2013.01);
(Continued)

(58) Field of Classification Search
USPC ......................................................... 607/88
See application file for complete search history.

(56) References Cited

U.S. PATENT DOCUMENTS 3,307,553 A    3/1967  Liebner
5,342,411 A    8/1994  Maxted et al.
(Continued)

FOREIGN PATENT DOCUMENTS

CN    108403288       8/2018
DE    44 04 213 A1    8/1995
(Continued)

OTHER PUBLICATIONS

Communication of Acceptance issued in Finnish Patent Application No. 20185775 dated Oct. 30, 2020.
(Continued)

*Primary Examiner* — Aaron F Roane
(74) *Attorney, Agent, or Firm* — Nixon & Vanderhye

(57) ABSTRACT

Disclosed is an applicator device for an apparatus used in a localized cryotherapy treatment. The applicator device is configured, when positioned over a body area to be treated, to receive and to uniformly distribute across the entire area covered thereby a stream of medium, such as air, adjusted to a temperature equal to or above −40 degrees Celsius (° C.) and directed, at a predetermined speed, via the applicator to the area to be treated, whereby a cold-induced thermal shock response is developed in skin and an underlying tissue within the area covered by the applicator. Related apparatus and a method are further provided.

17 Claims, 4 Drawing Sheets

(52) U.S. Cl.
CPC . *A61F 2007/0003* (2013.01); *A61F 2007/006* (2013.01); *A61F 2007/0011* (2013.01); *A61F 2007/0032* (2013.01); *A61F 2007/0035* (2013.01); *A61F 2007/0042* (2013.01); *A61F 2007/0044* (2013.01); *A61N 2005/0647* (2013.01); *A61N 2005/0652* (2013.01); *A61N 2005/0663* (2013.01)

(56) References Cited

U.S. PATENT DOCUMENTS

| | | |
|---|---|---|
| 2004/0243026 A1 | 12/2004 | Toepfer et al. |
| 2007/0118098 A1 | 5/2007 | Tankovich |
| 2008/0077213 A1 | 3/2008 | Vickroy |
| 2008/0281307 A1 | 11/2008 | Donahue |
| 2013/0238042 A1* | 9/2013 | Gildersleeve ......... A61F 7/0085 607/3 |
| 2014/0155962 A1 | 6/2014 | Deroberts |
| 2014/0303697 A1* | 10/2014 | Anderson ............. A61F 7/0085 607/104 |

FOREIGN PATENT DOCUMENTS

| | | |
|---|---|---|
| EP | 0 898 473 | 3/1999 |
| WO | 97/42919 | 11/1997 |

OTHER PUBLICATIONS

International Search Report for PCT/EP2019/074838 dated Nov. 26, 2019, 6 pages.
Written Opinion of the ISA for PCT/EP2019/074838 dated Nov. 26, 2019, 10 pages.

\* cited by examiner

APPLICATOR DEVICE AND RELATED APPARATUS

This application is the U.S. national phase of International Application No. PCT/EP2019/074838 filed Sep. 17, 2019 which designated the U.S. and claims priority to FI Patent Application No. 20185775 filed Sep. 18, 2018, the entire contents of each of which are hereby incorporated by reference.

FIELD OF THE INVENTION

The present invention relates to apparatuses and systems for carrying out local cryotherapy. In particular, the invention concerns an improved applicator device for such an apparatus, which applicator device allows for attaining a cold-induced thermal shock response in skin and underlying tissue at relatively high temperatures. Related apparatus, method and use are further provided.

BACKGROUND

Local (localized) cryotherapy is advantageous in terms of delivering benefits of a whole-body cryotherapy locally by targeting specific areas of the patients' body. In particular, cryotherapy treatment of specific body areas is recommended after orthopedic surgery and sports injuries to reduce pain, swelling and/or inflammation. Targeted cooling further invokes and/or reactivates internal resources of the organism, thus promoting its natural capacity for a self-defense against various diseases including asthma, hormone deficiencies, joint inflammation and skin disorders, such as allergies and psoriasis.

Cryotherapy treatment aims at inducing, in patients' skin and an underlying (soft) tissue, a thermal (cold) shock response, thereupon the aforementioned (cryo)therapeutic effect(s) take place. Thermal shock response is induced upon a sudden cold impact onto a particular body area, whereby the body develops local stress response, followed by activation of metabolic processes, acceleration and intensification of blood circulation, increased oxygen supply to blood and tissues and release of anti-inflammatory and analgesic substances, that altogether results in an at least alleviation of pain, reduced swelling and diminished muscle tension. Long-term effects of cryotherapy include an enhanced immune resistance of the organism and an improved flexibility and elasticity of soft tissues and skin. Cold treatments also promote cell replacement processes naturally occurring within the body, and elimination of dead cells, accordingly.

In conventional cryotherapy methods the patient is exposed to an impact of the extreme temperatures, such as below −100 degrees Celsius (typically within a range of −110 to −170° C.), for short time spans, typically 0.5-3 minutes at a time. In these methods, the required (cryo) therapeutic effect is achieved by using cryogenic coolants, such as (liquefied) carbon dioxide ($CO_2$) and liquid nitrogen ($LN_2$). Cryogenic coolant is blown over an entire patient's body (cryosauna) or onto relevant body parts (localized therapy) by means of compressed air or by pressure created upon evaporation and boiling of the liquid gas. In some instances, liquid gas is pumped from an unpressurised Dewar vessel with a cryopump.

However, there are certain (high) cost-, handling-, such as (re)filling, for example, storage (in pressurized containers or at extremely low temperatures) and transportation issues associated with the use of these materials. Accordingly, storage premises for said cryogenic coolants must be properly ventilated and continuously monitored, as to prevent accumulation of said gases to hazardous levels.

A number of systems further exist, in which air chilled down to about minus 30 degrees Celsius is blown onto particular regions of the patients' body. In these systems cold air is used as a local anesthetic upon conducting primarily esthetic/cosmetic treatments, such as laser-, Intense Pulsed Light- (IPL) and High-Intensity Focused Ultrasound- (HIFU) treatments, as well various injection treatments (Botox, dermal fillers, and the like).

Applicability of the aforesaid systems in cryotherapy is hindered due to insufficient cooling power produced thereby. Thus, although cold air is delivered onto a predetermined area on the patients' skin via a hose, the temperature of the air stream that actually reaches the patients' skin is too high to generate the cold-induced thermal shock response indispensable for achieving the (cryo)therapeutic effect(s). It is evident that in an absence of the thermal shock response, the treatment cannot be considered therapeutic in a sense of imposing healing and/or health-promoting effects onto an individual.

Additionally, it should be noted that ability to withstand cold largely varies amongst individuals. Some patients could not fully benefit from cryotherapy treatments due to personal cold intolerance. Moreover, targeting the extreme cold impact specifically onto sensitive areas, such as face, is associated with the risk of cold injury and it is intolerable by merely all individuals.

In this regard, it is still desirable to complement and update the field of technology related to cryotherapy, and to develop a simple and efficient solution for expanding cold impact related treatments to all groups of patients in a cost-effective manner.

SUMMARY OF THE INVENTION

An objective of the present invention is to solve or at least mitigate each of the problems arising from the limitations and disadvantages of the related art. The objective is achieved by various embodiments of an applicator device for an apparatus used in a localized cryotherapy treatment, according to what is defined in the independent claim 1. In preferred embodiment, the applicator device is configured, when positioned over a body area to be treated, to receive and to uniformly distribute across the entire area covered by said applicator a stream of gaseous medium, such as air, adjusted to a temperature equal to or above −40 degrees Celsius (° C.), preferably, within a range of −40 to −15 degrees Celsius (° C.), still preferably, within a range of −25 to −20° C., and directed, at a predetermined speed, via said applicator to the area to be treated, whereupon a cold-induced thermal shock response is developed in skin and an underlying tissue within the area covered by said applicator.

In some embodiments, the applicator device is configured to cover and/or to enfold around the area to be treated. In some further embodiments, the applicator device is configured to be brought into contact with the area to be treated through an innermost surface or a surface layer thereof.

In some embodiments, the applicator device is further configured to receive and distribute the stream of gaseous medium directed thereto at a speed within a range of 5 to 17 meters per second (m/s).

In some embodiments, the applicator device is configured foldable.

In some embodiments, the applicator device further comprises fastening means for securing said applicator device around the area to be treated.

In some embodiments, the applicator device is configured to be positioned over the body area selected from the group consisting of the: wrist, elbow, shoulder, scapula-bone area, neck, knee, and ankle. In some other embodiments, the applicator device is configured to be positioned over a patients' face.

In some other embodiments, the applicator device further comprises a number of light sources at the internal surface thereof. Said light sources can be configured as variable wavelength light sources.

In some embodiments, the applicator device further comprises an additional layer with a plurality of apertures, said layer arranged such, that a gap is established between the internal surface of the applicator device and said additional layer, whereby the stream of gaseous medium received into said gap is uniformly distributed, via the apertures provided in the additional layer, across the entire area to be treated covered by said applicator device.

In another aspect, an apparatus for use in a localized cryotherapy treatment is provided according to what is defined in the independent claim 13.

In embodiments, the apparatus comprises an at least one applicator device and a blower unit, wherein the blower unit us configured to generate and to direct, at a predetermined speed, a stream of gaseous medium adjusted to a temperature equal to or above $-40$ degrees Celsius (° C.) to the at least one applicator device, and wherein said at least one applicator device is configured, when positioned over a body area to be treated, to receive and to uniformly distribute across the entire area covered by said applicator device the stream of gaseous medium directed thereto from the blower unit, whereby a cold-induced thermal shock response is developed in skin and an underlying tissue within the area covered by said applicator device.

In some embodiments, the stream of gaseous medium generated by the blower unit of the apparatus is directed to the spatially restricted body area at a speed within a range of 5 to 17 meters per second (m/s).

In preferred embodiments, the stream of gaseous medium generated by the blower unit is air.

In a still further aspect, use of the applicator device and/or of the apparatus according to some previous aspects is provided, according to what is defined in the independent claim 17, in a non-invasive treatment by cryotherapy, optionally, combined with a light therapy.

In embodiments, use is provided, wherein a stream of gaseous medium adjusted to a temperature equal to or above $-40$ degrees Celsius (° C.) is directed, at a predetermined speed, from a blower unit to a spatially restricted body area via the applicator device configured, when positioned over said body area, to receive and to uniformly distribute across the entire area covered by said applicator device the stream of gaseous medium directed thereto from the blower unit, whereby a cold-induced thermal shock response is developed in skin and an underlying tissue within the area covered by said applicator device In embodiments, said use further comprises activating a number of light sources provided at an internal surface of the applicator device.

The utility of the present invention arises from a variety of reasons depending on each particular embodiment thereof. On the whole, the invention allows for effectively targeting specific body areas by localized cold treatment(s), whereupon the (cryo)therapeutic effect or effects stipulated by generation of the cold-induced thermal shock response are achieved within a particular area to be treated, at temperatures much higher than that utilized for conventional cryotherapy. By means of the applicator device, provided hereby, the cold-induced thermal shock response within a spatially restricted body area is developed already at subzero temperatures within a range of 25-20 degrees Celsius ($-25°$ C. to $-20°$ C.). This creates prerequisites for effectively conducting cold therapy treatments on patients with low perception threshold for cold and/or on the cold-sensitive areas within the patient's body, such as face-, neck and/or tendon areas.

The invention is based on a so called "wind chill factor" principle (whereby the body fees far colder than the ambient temperature due to the wind/the flow of cold air) together with the containment of the cooling medium stream, in order to maximize heat extraction capacity from skin and subcutaneous tissue within the treated area.

The invention does not strictly require utilization of cryogenic coolants (liquid gases); however utilization of the latter is not excluded. In fact, the invention allows for attaining healing- and/or health-promoting benefits typically associated with invoking the thermal shock response by exposing the patient to extremely low temperatures ($-100$ degrees Celsius and lower) at the aforesaid "high" temperatures. Additionally, flexible design of the applicator device provided hereby enables cryo-treatments around the predetermined body area, such as an entire joint (shoulder-, elbow- or knee-joint), for example, thus encompassing a spatial range of 360°.

Moreover, the invention is easily combinable with other health-related technologies, such as light therapy (phototherapy) methods, for example. Thus, treatments by cryotherapy and LED Photon therapy can be simultaneously conducted on the treated area. In this regard, the invention provides a powerful tool for treating a variety of dermal infections, such as acne and related skin inflammations. Due to simultaneously pursued at least "double impact" (e.g. cold and light), an overall number of treatments required to combat a dermal disease could be reduced, which allows decreasing treatment-associated costs borne by the patient, accordingly.

Terms "local" and "localized" are utilized in present disclosure interchangeably to indicate a treatment targeted to a particular area of the patients' body.

The expression "a number of" refers in present disclosure to any positive integer starting from one (1), e.g. to one, two, or three. The expression "a plurality of" refers to any positive integer starting from two (2), e.g. to two, three, or four.

Different embodiments of the present invention will become apparent by consideration of the detailed description and accompanying drawings.

DETAILED DESCRIPTION OF THE EMBODIMENTS

Figure 1A:
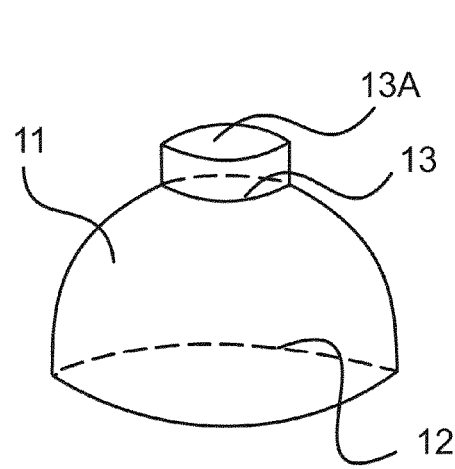
FIG. 1A illustrates an applicator device, according to some embodiment.

Detailed embodiments of the present invention are disclosed herein with the reference to accompanying drawings. The same reference numerals are used throughout the drawings to refer to same members as follows:

10, 10A, 10B, 10C—an applicator device;
11—an external surface of the applicator device;
12—an internal surface of the applicator device;
12A—an additional layer;
12B—a gap established between the internal surface 12 and the additional layer 12A;
13, 13A—an inlet, and an inlet adapter, accordingly (for the applicator device);
14A, 14B—fastening means;
15—apertures in the applicator device for eyes, nose and mouth;
16—light sources;
17, 17A—a connection interface and a power supply device, accordingly;
18—apertures in the additional layer 12A;
19—a connector;
20—a blower unit;
21—a control terminal;
22—a blowpipe;
23—an adapter (for the blower unit);
31—a stream of gaseous medium;
100—an apparatus for use in a localized cryotherapy treatment.

FIGS. 1-3 illustrate at 10 a concept underlying various embodiments 10A, 10B and 10C of an applicator device (a treatment head) in accordance with some aspect of the present invention. The applicator device, hereafter the "applicator", is provided for an apparatus used in a localized cryotherapy treatment, i.e. for the cryotherapy treatment that targets particular areas of the patients' body.

Upon said cryotherapy treatment a controlled cold impact is applied onto a predetermined body area, whereby a cold-induced thermal shock response (cold shock response) is developed in patients' skin and the underlying tissue, such as subcutaneous tissue, within a spatially restricted area. For clarity purposes the expression "cold-induced thermal shock response" is utilized in the present disclosure with reference to the processes occurring in skin and the underlying tissue during and instantly after the controlled cold impact, which processes include, but are not limited to: vasomotor response, such as cold-induced alteration of the diameter in peripheral blood vessels (hereby, narrowing or vasoconstriction and subsequent widening or vasodilation) leading to acceleration and intensification of blood circulation and increased oxygen supply to blood and tissues; and release into bloodstream of the neuromediator substances, such as noradrenaline, serotonin and endorphins, for example. Amongst aforesaid, noradrenaline in known for its involvement in reducing inflammation processes; whereas serotonin and endorphins are often referred to as natural painkillers.

The applicator device 10A, 10B, 10C described hereinbelow is configured for human patients. Nevertheless, upon appropriate modifications, said applicator device is fully applicable also to nonhuman mammals, in particular, so called companion animals and pets, such as dogs, horses, and the like.

The applicator 10A, 10B, 10C is advantageously configured to be positioned over a body area to be treated. The area to be treated is a predetermined area on the patients' body intended to be covered and/or contained by said applicator device. The applicator device is further configured to receive a stream of gaseous medium, such as air, adjusted to a predetermined temperature and to uniformly distribute said gaseous medium stream across the entire area covered thereby (the area to which cold treatment is targeted) such, that the gaseous medium stream is directed, via said applicator device, towards the area to be treated at a predetermined speed. It is preferred that the stream of gaseous medium, such as air, is adjusted to the temperature equal to minus 40 (−40) or above degrees Celsius (° C.), preferably, within a range between minus 40 (−40) and minus 15 (−15) degrees Celsius, still preferably, within a range between minus 25 (−25) to minus 20 (−20) degrees Celsius. Although the present disclosure concerns air as a primary gaseous medium, use of other gaseous media is not excluded, when appropriate.

By placement of the applicator device over the predetermined body area, a closed- or an essentially closed volume is established, whereupon the cold-induced thermal shock response is developed in skin and the underlying tissue within the area covered by said applicator. Cooled air delivered into said closed or essentially closed volume is forced to remain within the area covered by the applicator; thereby uniform distribution of cold air across the entire area to be treated (hereby, the area covered by the applicator) is attained. In existing systems, in which cold air is blown, through a hose, onto a particular spot on the skin, uniform distribution of cold air across the entire treatment area cannot be achieved due to dissipation of said cold air prior it reaches the skin (the hose is never pushed against the skin).

Development of the cold-induced thermal shock response within the area to be treated is further accounted for directing the stream of gaseous medium, such as air, via the applicator, towards the area to be treated at a predetermined speed. Optimal velocity range for the air flow at which the applicator device effectively receives and uniformly distributes the stream of air directed thereto constitutes 5-17 meters per second (m/s). Thus, at a speed of air flow being 16 m/s (air flow velocity), the amount of air that flows through the applicator device (air flow capacity) constitutes 75 cubic meters per hour (m$^3$/h).

Hence, development of the cold-induced thermal shock response within the area to be treated is stipulated by the following factors: velocity of air flow, capacity of air flow and provision of the applicator device 10A, 10B, 10C, according to the embodiments disclosed hereinbelow. In preliminary trials, the applicators embodied as 10A, 10B, 10C persuasively demonstrated development of said cold-induced thermal shock within a predetermined area to be treated within a time period of 90-180 seconds (s), wherein air flow velocity constituted 16 m/s, thus providing for the air flow capacity 75 m$^3$/h.

It is preferred that, when positioned over the patients' skin, the applicator 10A, 10B, 10C covers and/or to enfolds around the area to be treated.

The applicator 10A, 10B, 10C comprises a body with an external surface 11 and an internal surface 12 (FIGS. 1-3). The body of said applicator is preferably manufactured from shape-retaining polymeric materials. Depending on an embodiment, the applicator can be manufactured from stiff polymeric materials and/or from essentially flexible, resilient materials. By stiffness we refer hereby to a measure of rigidity of the material, defined by ability thereof to withstand bulk deformation in response to applied force. Accordingly, by flexibility/resilience we refer to the ability of the material to flex upon impact, whereby material is deformable by pressing, bowing, bending, twisting, turning, and the like, without breaking or getting damaged.

The applicator 10A, 10B, 10C further comprises an at least one inlet 13 to receive the gaseous medium, such as air, wherein each inlet 13 is advantageously equipped with an appropriate adapter 13A and optionally a connecting means 19 to mediate connection of said applicator to a blowpipe provided within a blower unit, such as an air blower unit (not shown). By means of the adapter 13A the applicator 10A, 10B, 10C can be easily detached from, replaced and attached to the same blowpipe. The adapter 13A and/or the connecting means 19 thus enable replacing the applicator 10A by the applicators 10B or 10C, depending on the area intended for treatment.

With regard to the applicator device 10, the adapter 13A may be built-in or detachable. The connection between said adapter 13A and the blowpipe can be implemented via screw-thread connectors, "plug-in" connectors, U- or Y-type connectors, or any other type of connector capable to provide a stable air flow (at a predetermined speed) between the air blower unit and the applicator device 10.

FIG. 1A shows a basic configuration of the applicator device referenced as 10A. The applicator 10A is provided in the form of a hemisphere (cup- or dome-shaped) in a number of different sizes with diameter varying between 70-200 mm and height varying between about 50-100 mm, accordingly. Thus, an exemplary "medium size" applicator 10A designed especially for treating knees and shoulders has about 125 mm in diameter and about 70 mm in height. The same can be provided in smaller- and larger sizes for treating e.g. elbows (small size applicator; diameter 70-110 mm; height 50-60 mm) and neck-and-back area (large size applicator; diameter 150-200 mm; height 80-100 mm). The applicator 10A can be manufactured from either stiff or flexible polymeric materials, in accordance to what is described hereinabove.

Provision of the applicator 10A is such, as to be advantageously positioned over joint areas, such as elbow-, shoulder- and knee-joint areas, and over the essentially flat areas, such as neck-and-back area (scapula-bone area), for example.

Figures 2A, 2B:
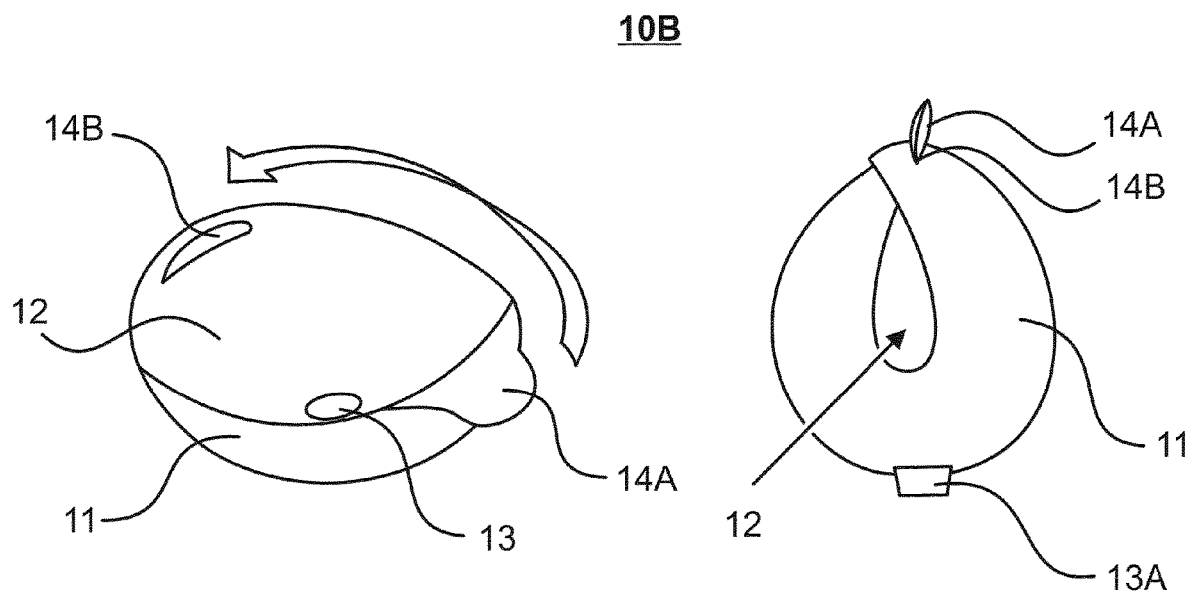
FIGS. 2A and 2B illustrate an applicator device according to some other embodiments, in unfolded and folded states, accordingly.

FIGS. 2A and 2B illustrate, at 10B, another configuration for the applicator device, in accordance with the present invention, in unfolded- and folded state, accordingly. The applicator device 10B is preferably configured foldable. Said applicator 10B is preferably manufactured from flexible, resilient material to be placed such, as to enfold around the area to be treated. In preferred configurations the applicator 10B is made of silicon polymers. Other materials include, but are not limited to low-density polyethylene, ethylene-vinyl acetate, thermoplastic elastomers, and the like.

In preferred configurations the applicator 10B is essentially hemisphere- or cup-shaped (unfolded state, FIG. 2A) such, as to advantageously encompass a joint area, e.g. knee- or elbow joints. In some alternative configurations the applicator 10B can provided pad-shaped or in the form of an elliptical hemisphere (a half of a rugby ball), for example. Such pad-shaped applicator can be advantageously utilized to wrap around limbs or tendons, such as Achilles tendon, and the like.

The applicator device 10B is preferably provided with fastening means 14, such as an edge overhang/projection 14A and an aperture 14B to receive said projection and positioned opposite thereto. It is clear that any alternative fastening means (e.g. buttons, cords, self-adhesive surfaces, etc.) are not excluded.

With reference to FIG. 2A, the applicator 10B, when positioned over the area to be treated, e.g. an elbow, is further enfolded (wrapped or rolled) therearound such, that an entire area to be treated (hereby, the elbow joint) is covered by said applicator. Enfolding (wrapping or rolling) direction is shown on FIG. 2A by an arrow. The applicator 10B is further secured around the area to be treated by the fastening means 14 (FIG. 2B) such, that the limb (hereby, the arm) accommodates in the space indicated, on FIG. 2B, by the reference numeral 12 (as adjoining the innermost surface of the applicator device). The applicator 10B thus makes a full contact with the area to be treated through the internal surface 12 thereof, wherein said internal surface 12 establishes the innermost surface of the applicator.

Provision of the applicator 10B is hereby such, as to be advantageously positioned over joint- and tendon areas (e.g. elbow-, shoulder-, knee-, wrist- and ankle joints and tendons).

Figure 3A:
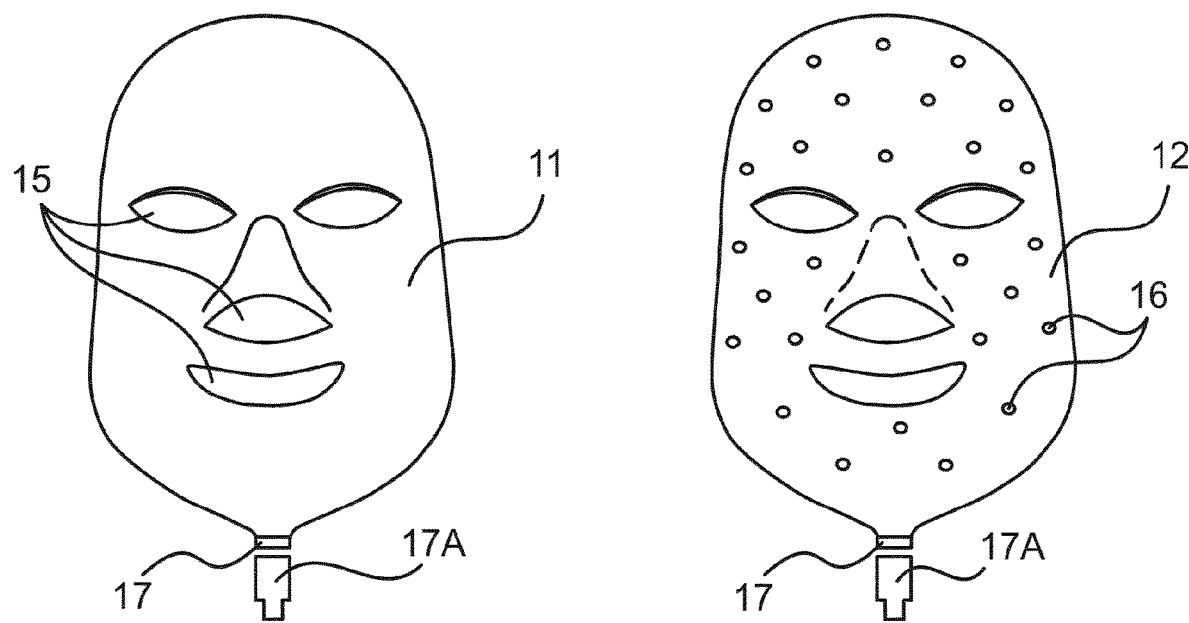
FIG. 3A illustrates an applicator device, according to still another embodiment, viewed from the outside (external surface; left) and from the inside (internal surface; right). Right view does not include an innermost surface layer.

A reference is further made to FIG. 3A that shows the applicator device 10C configured to be positioned over a patients' face and provided in the form of a face mask, accordingly. FIG. 3A shows the external surface 11 of the applicator 10C (left) and the internal surface 12 thereof (right).

It is preferred that the applicator 10C additionally comprises a number of light sources 16 positioned at the internal surface 12 thereof. The light sources 16 can be mounted onto said internal surface 12 or alternatively provided on an appropriate support (not shown). Said light sources are advantageously disposed across the entire inner surface 12 (FIG. 3, right) of the applicator 10C, individually or in arrays; however, any appropriate configuration is not excluded such, as to cover only a predetermined part of the face, for example.

The light sources are preferably Light Emitting Devices (LEDs). Nevertheless, it should be clear that, in view of the development of technology, any appropriate light source can be utilized in the applicator 10C. Each said light source 16 is advantageously configured to emit light within a predetermined portion of the electromagnetic spectrum, preferably, within the visible spectrum, defined as the wavelength range of electromagnetic radiation between 380 and 750 nanometers (nm). In some instances, each light source can be configured to emit light at a single fixed wavelength, such as blue (about 490 nm to about 450 nm), green (about 560 nm to about 520 nm) and/or red (about 620 nm to about 750 nm). Within the applicator 10C, combining light sources configured to emit light at different wavelengths into arrays is advantageous in terms of providing facial treatments intended to target a particular dermal condition.

Thus, blue light is known to effectively treat a variety of dermal infections, such as acne and related skin inflammations. Green light is, in turn, known to targets dark circles, pigmentation, and the like. Additionally, green light calms irritated skin and it is often used in the anti-age treatments. Red light accelerates blood circulation at skin surface and increases collagen production, which is essential for various skin stimulation- and rejuvenation (cosmetic) treatments.

It is further preferred that the light sources 16 within the applicator 10C are configured as variable wavelength light sources, thereupon wavelength range emitted by a single light source can be adjusted within predetermined limits. Thus, the light source(s) 16 can be configured as RGB LEDs (Red-, Green- and Blue LEDs) that combine three light emitting diode units in one package. Within said RGB LED, it order to produce light of a predetermined wavelength (e.g. blue), an appropriate LED unit must be activated having another two units switched off. RGB configuration allows for "mixing" lights by combining these three colors in different intensities. For the sake of completeness, since the RGB LEDs are generally known from the art, we provide no further details on that subject.

The applicator 10C further comprises a connection interface 17 configured to mediate delivery of electric power to the light sources 16. An exemplary interface 17 can be configured as a port or an adapter to receive a power supply device 17A, such as an USB power supply, for example.

Figure 3B:
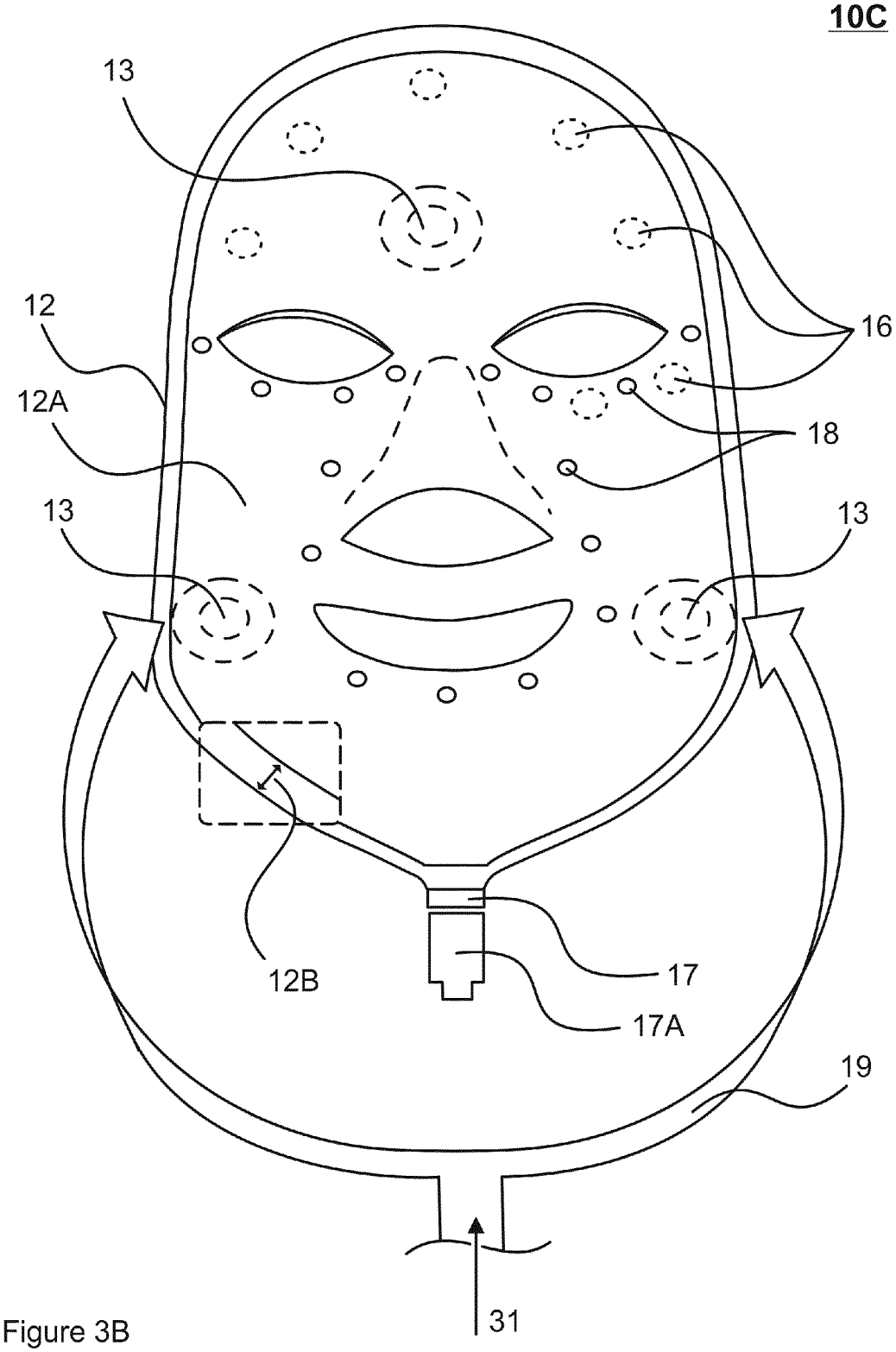
FIG. 3B illustrates the same applicator device as FIG. 3A, viewed from the inside and in the presence of the innermost surface layer.

The reference is further made to FIG. 3B that shows, from the inside, the applicator 10C fully assembled. In preferred configurations, the applicator 10C further comprises an additional layer 12A adjacent to the internal surface 12 of the applicator body. By said layer 12A the innermost surface of the applicator 10C is established, by which surface said applicator is brought into contact with the entire area to be treated, hereby, the face.

The innermost layer 12A comprises a plurality of apertures 18. Said apertures 18 are preferably disposed across the entire layer 12A; however, in some instances, the apertures 18 may be arranged into the rows and/or arrays and disposed in predetermined locations. It is further preferred that the light sources 16 (dashed circles) provided at the internal surface 12 of the applicator body and the apertures 18 provided in the additional layer 12A do not superimpose.

The layer 12A is arranged such, that a gap or an air distribution channel 12B is established between the internal surface 12 of the applicator body and said innermost layer 12A. The distance defined by said gap 12B between the surfaces 12 and 12A is provided within a range of 2-10 mm, preferably, 4-7 mm. The stream of air 31 directed from the air blower unit (not shown) is thus received into said gap 12B, wherefrom said air stream is uniformly distributed, via the apertures 18, across the entire treatment area covered by the applicator device 10C.

By varying the number, disposition and/or dimensions of the apertures 18, it is further possible to target specific subareas (e.g. area around eyes, cheeks, forehead) within the treatment area (face) covered by the applicator 10C. For example, the apertures can be configured variable in terms of (2D) shape (circular, elongated, etc.) and/or in terms of 3D configuration (aperture provided as a cylindrical- or conical through-channel, etc.).

The air stream 31 is received into the applicator 10C (into the gap 12B) via a number of inlets 13. Number of inlets 13 may vary; however, it is preferred that at least two inlets are provided sideways (right and left) to ensure uniform air supply into the applicator 10C via the dual inlet arrangement implemented by means of an exemplary branched connecting means 19, such as Y- or U-connector, for example. FIG. 3B shows an exemplary configuration with three inlets 13, wherein, in addition to side inlets functionally joined by the Y-connector 19, air supply is further realized via the inlet disposed within the forehead area of the applicator 10C.

In some instances, the applicator 10C is further equipped with a number of control valves, such as electric solenoid valves, for example (not shown), to control the direction, volume and speed (velocity) of the air flow. Said control valves are preferably operated via the user interface. Pre-set valve parameters enable default settings for implementing different treatment protocols, including, but not limited to: an eye area treatment, a cheek treatment, a headache treatment, and the like.

The applicator 10C further comprises a number of apertures 15 for eyes, nose and/or mouth. The additional layer 12A is hereby joined with the applicator body at the borders defined by the apertures 15 and along the outer edge of the applicator 10C. Such arrangement allows for creating an essentially closed volume, wherefrom cooled air, supplied into the applicator solely through the inlets 13, is further uniformly distributed across the entire treatment area (hereby, the face). It is further preferred that the inlets 13 are provided essentially in between the adjacent surfaces 12 and 12A (the inlets 13 are shown on FIG. 3B by dashed circles, as seen "through" the layer 12A).

As evident from FIGS. 3A and 3B, the applicator 10C is further shaped such, as to encompass prominent areas of the patient face, such as nose, chin, and the like.

It is preferred that the body of the applicator 10C is manufactured from stiff polymeric materials, whereas the innermost (apertured) layer 12A is manufactured from flexible polymeric materials, in accordance to what is described hereinabove, to ensure safety and comfort of the patient.

It is further preferred that each applicator 10A, 10B, 10C is further equipped with an at least one thermal sensor/transmitter (not shown), configured to measure skin temperature during the cold treatment and/or send measurement data to a central processing unit or the like. Provision of additional sensor device(s) for measuring other parameters, such as humidity, for example, is not excluded.

Figure 4:
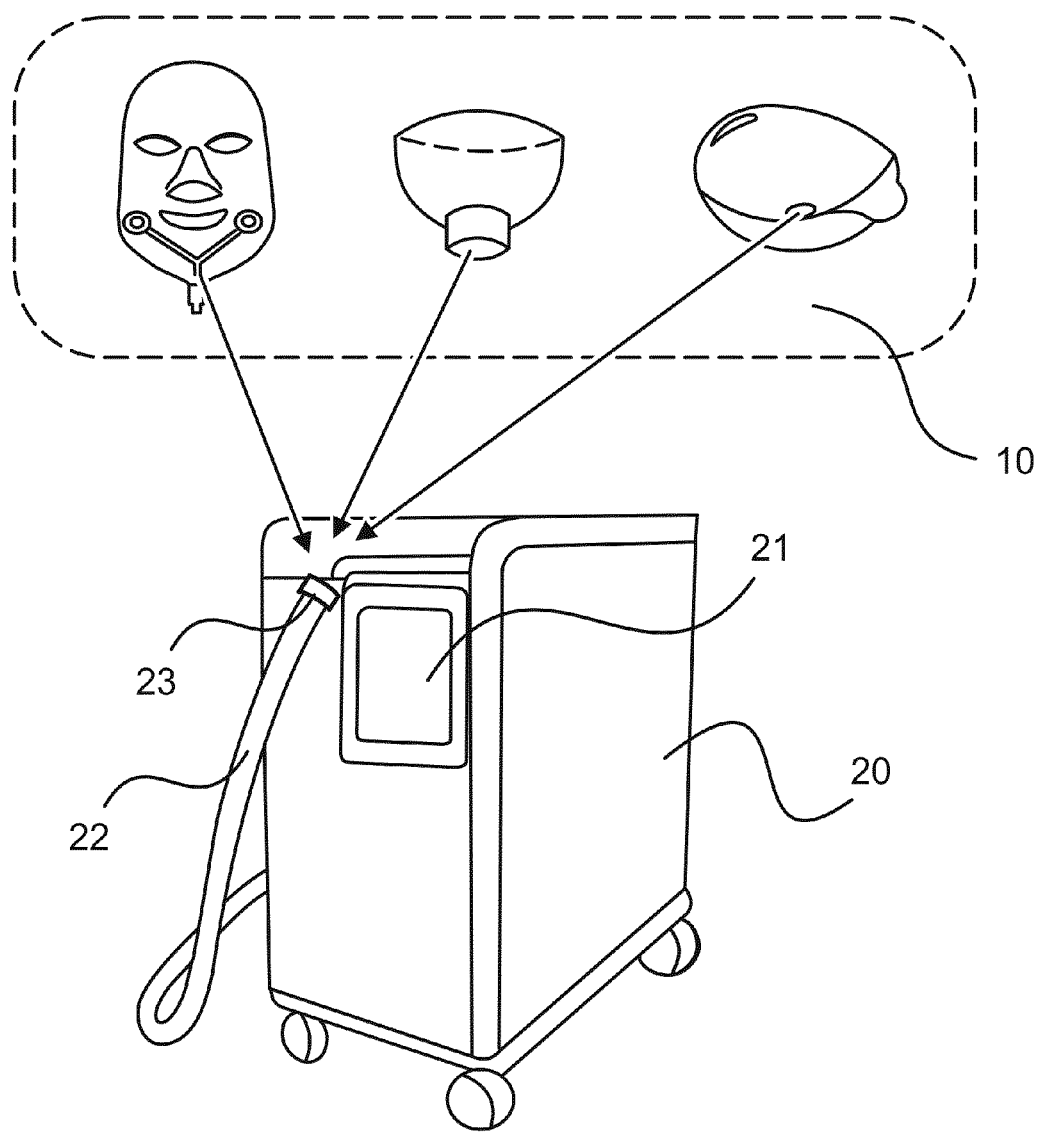
FIG. 4 illustrates an apparatus for use in a localized cryotherapy treatment, according to various embodiments.

FIG. 4 illustrates an apparatus 100 for use in a localized cryotherapy treatment, according to another aspect. The apparatus 100 comprises an at least one applicator device 10 embodied as any one of 10A, 10B, 10C, in accordance to the description above, and a blower unit 20, configured as an air blower unit, for example. Said blower unit 20 is preferably configured to generate a stream of gaseous medium, such as air adjusted to a predetermined temperature equal to or above −40 degrees Celsius (° C.), preferably, within a range of −40 to −15° C., still preferably, within a range of −25 to −20° C., and to direct said stream of air to the at least one applicator device 10, via a blowpipe 22. Any conventional air blower unit 20 having capacity for generating an air stream at a speed within a range of 5-16 meters per second (m/s) can be utilized hereby.

Each blowpipe 22 further comprises an adapter 23 to ensure additional compatibility of said blowpipe (typically standard-sized) with the applicator 10 (10A, 10B, 10C) via the corresponding adapter 13A and/or the connecting means 19.

The apparatus 100 advantageously comprises a control terminal 21 equipped with a user interface, preferably, a graphical user interface. Via said user interface the operator performs selection of the area(s) to be treated and adjusts treatment-related parameter values, such as duration, temperature- and velocity of the air flow, to comply with the patient-related values, such as patients' age, gender and body weight. The abovementioned values are preferably stored in the apparatus 100 or on an external storage medium (not shown) in a form of a patient-specific data set, for example.

Thus, time-related parameters vary depending on the area to be treated and the body mass (body weight) of a patient. For example, cold treatment, associated with the development of the cold-induced thermal shock response, of a knee-joint with regard to a patient who weighs 60 kg takes about 90 s; whereas the same with regard to a patient who weighs 120 kg may take 240 s or even longer.

In some embodiments, the apparatus 100 and/or the applicator device (10, 10A, 10B, 10C) are used in a method for producing a cold-induced shock response within a spatially restricted body area. In the procedure, a stream of gaseous medium, such as air, adjusted to a temperature equal to or above −40 degrees Celsius (° C.), preferably, within a range of −40 to −15° C., still preferably, within a range of −25 to −20° C., is thus directed, at a predetermined speed, from the (air) blower unit 20 to a predetermined body area via the applicator 10 embodied as any one of 10A, 10B, 10C. The applicator 10 is, in turn, configured, when positioned over the body area, to receive and to uniformly distribute across the entire area covered by said applicator the stream of gaseous medium, such as air, directed thereto from the (air) blower unit, whereby a cold-induced thermal shock response is developed in skin and an underlying tissue within the area covered by said applicator.

It is further preferred that said stream of gaseous medium is directed to the spatially restricted body area (area to be treated) at a speed within a range of 5-17 m/s.

In some embodiments, in particular, for those involving the applicator 10C, the procedure further comprises activating a number of light sources 16 disposed at an inner surface 12 of the applicator device by plugging the power supply device 17A into the port or the adapter 17, for example, and enabling electric power supply thereto.

In some further aspect, use of the applicator 10A, 10B, 10C in a non-invasive treatment by cryotherapy, optionally, combined with a light therapy (phototherapy), such as LED Photon therapy.

It is clear to a person skilled in the art that with the advancement of technology the basic ideas of the present invention may be implemented in various ways. The invention and its embodiments may generally vary within the scope of the appended claims.

The invention claimed is:

1. An apparatus configured for use in a localized cryotherapy treatment, said apparatus comprising:
at least one applicator device comprising
a plurality of light sources at an internal surface of the applicator device, the plurality of light sources being configured as variable wavelength light sources; and
a blower configured to generate and direct, at a predetermined speed, within a range of 5 to 17 meters per second, a stream of gaseous medium adjusted to a temperature within a range of −40 to −15 degrees Celsius to the at least one applicator device,
wherein said at least one applicator device is configured, when positioned over a body area to be treated, to receive and to uniformly distribute, across the entire area covered by said at least one applicator device, the stream of gaseous medium directed thereto from the blower, whereby a cold-induced thermal shock response is developed in skin and an underlying tissue within the body area covered by said at least one applicator device.

2. The apparatus of claim 1, wherein the stream of gaseous medium generated by the blower is adjusted to a temperature within a range of −25 to −20 degrees Celsius.

3. The apparatus of claim 1, wherein the stream of gaseous medium generated by the blower is air.

4. An applicator device for an apparatus used in a localized cryotherapy treatment, the applicator device comprising:
a plurality of light sources at an internal surface of the applicator device, the plurality of light sources being configured as variable wavelength light sources,
wherein said applicator device is configured, when positioned over a body area to be treated, to receive and to uniformly distribute, across the entire area covered by said applicator device, a stream of gaseous medium adjusted to a temperature within a range of −40 to −15 degrees Celsius and directed, at a predetermined speed, within a range of 5 to 17 meters per second, via said applicator device to the area to be treated, whereby a cold-induced thermal shock response is developed in skin and an underlying tissue within the body area covered by said applicator device.

5. The applicator device of claim 4, wherein the applicator device is configured to one or more of cover and enfold around the area to be treated.

6. The applicator device of claim 5, wherein the applicator device is configured to be brought into contact with the body area to be treated through an innermost surface thereof.

7. The applicator device of claim 5, wherein the applicator device is configured to receive and to distribute the stream of gaseous medium adjusted to a temperature within a range of −25 to −20 degrees Celsius.

8. The applicator device of claim 5, wherein the applicator device is configured to be foldable.

9. The applicator device of claim 4, wherein the applicator device is configured to be brought into contact with the body area to be treated through an innermost surface thereof.

10. The applicator device of claim 9, wherein the applicator device is configured to receive and to distribute the stream of gaseous medium adjusted to a temperature within a range of −25 to −20 degrees Celsius.

11. The applicator device of claim 9, wherein the applicator device is configured to be foldable.

12. The applicator device of claim 4, wherein the applicator device is configured to receive and to distribute the stream of gaseous medium adjusted to a temperature within a range of −25 to −20 degrees Celsius.

13. The applicator device of claim 4, wherein the applicator device is configured to be foldable.

14. The applicator device of claim 4, wherein the applicator device is configured to be positioned over the body area selected from the group consisting of: a wrist, an elbow, a shoulder, a scapula-bone area, a neck, a knee, and an ankle.

15. The applicator device of claim 4, further comprising a fastener configured to secure said applicator device around the body area to be treated.

16. The applicator device of claim 4, wherein the applicator device is configured to be positioned over a face of a patient.

17. The applicator device of claim 16, further comprising a layer with a plurality of apertures such that a gap is defined between the internal surface of the applicator device and the layer, whereby the stream of gaseous medium received into said gap is uniformly distributed, via the apertures, across the entire area covered by said applicator device.

* * * * *